US006592912B1

(12) United States Patent
Barabolak et al.

(10) Patent No.: US 6,592,912 B1
(45) Date of Patent: Jul. 15, 2003

(54) METHOD OF CONTROLLING RELEASE OF ANTIMICROBIAL AGENTS FROM CHEWING GUM AND GUM PRODUCED THEREBY

(75) Inventors: Roman M. Barabolak, Palos Park, IL (US); Steven E. Zibell, Tinley Park, IL (US); David L. Witkewitz, Bridgeview, IL (US); Michael J. Greenberg, Northbrook, IL (US); Robert J. Yatka, Orland Park, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 3 days.

(21) Appl. No.: 09/599,921

(22) Filed: Jun. 22, 2000

Related U.S. Application Data

(63) Continuation of application No. PCT/US97/24132, filed on Dec. 30, 1997.

(51) Int. Cl.⁷ ............................. A23G 3/30; A61K 9/68
(52) U.S. Cl. ............................. 426/3; 424/48; 424/440; 426/5
(58) Field of Search ............................. 426/3, 5; 424/48, 424/44

(56) References Cited

U.S. PATENT DOCUMENTS

| | | | |
|---|---|---|---|
| 4,624,849 A | 11/1986 | Toogood | 424/78 |
| 4,822,597 A | 4/1989 | Faust et al. | 424/48 |
| 4,853,212 A | 8/1989 | Faust et al. | 424/48 |
| 4,894,220 A | 1/1990 | Nabi et al. | 424/52 |
| 4,978,537 A | 12/1990 | Song et al. | 426/5 |
| 5,032,385 A | 7/1991 | Reed et al. | 424/49 |
| 5,037,637 A | 8/1991 | Gaffar et al. | 424/52 |
| 5,156,835 A | 10/1992 | Nabi et al. | 424/52 |
| 5,300,305 A | 4/1994 | Stapler et al. | 424/490 |
| 5,334,375 A | 8/1994 | Nabi et al. | 424/52 |
| 5,356,615 A | 10/1994 | Gaffar | 424/49 |
| 5,380,530 A | 1/1995 | Hill | 424/440 |
| 5,453,265 A | 9/1995 | Gaffar et al. | 424/52 |
| 5,472,685 A | 12/1995 | Gaffar | 424/49 |
| 5,474,761 A | 12/1995 | Liang | 424/52 |
| 5,487,902 A | 1/1996 | Andersen et al. | 426/3 |
| 5,496,540 A | 3/1996 | Gaffar et al. | 424/49 |
| 5,531,982 A | 7/1996 | Gaffar et al. | 424/49 |
| 5,560,906 A | 10/1996 | Scodari et al. | 424/54 |
| 5,693,334 A | 12/1997 | Miskewitz | 424/440 |
| 5,702,687 A | 12/1997 | Miskewitz | 424/52 |
| 5,711,961 A | 1/1998 | Reiner et al. | 424/441 |
| 6,248,309 B1 | 6/2001 | Iyer et al. | 424/49 |
| 6,436,369 B2 | 8/2002 | Barabolak et al. | 424/48 |

FOREIGN PATENT DOCUMENTS

| | | |
|---|---|---|
| EP | 0 399 479 | 11/1990 |
| ES | 2015656 | 5/1989 |
| JP | 92-139117 A | 5/1992 |
| WO | WO 84/03201 | 8/1984 |
| WO | WO 89/05590 | 6/1989 |
| WO | WO 90/11020 | 10/1990 |
| WO | WO 90/14015 | 11/1990 |
| WO | WO 91/03147 | 3/1991 |
| WO | WO 92/20319 | 11/1992 |
| WO | WO 99/33352 | 7/1999 |

Primary Examiner—Arthur L. Corbin
(74) Attorney, Agent, or Firm—Steven P. Shurtz; Brinks Hofer Gilson & Lione

(57) ABSTRACT

A method for producing a chewing gum with a controlled release of an antimicrobial agent, as well as the chewing gum so produced, is obtained by physically modifying the release properties of the antimicrobial agent by coating and drying. The antimicrobial agent is coated by encapsulation, partially coated by agglomeration, entrapped by absorption, or treated by multiple steps of encapsulation, agglomeration, and absorption. The coated antimicrobial agent is preferably then co-dried and particle sized to produce a release-modified antimicrobial agent for use in chewing gum. When incorporated into the chewing gum, these particles are adapted to produce a fast release or a delayed release when the gum is chewed. The preferred antimicrobial agent is chlorhexidine digluconate.

26 Claims, No Drawings

METHOD OF CONTROLLING RELEASE OF ANTIMICROBIAL AGENTS FROM CHEWING GUM AND GUM PRODUCED THEREBY

CROSS REFERENCE TO RELATED APPLICATION

The present application is a continuation of PCT application Serial No. US 97/24132 filed Dec. 30, 1997 and designating the United States, which is hereby incorporated by reference.

BACKGROUND OF THE INVENTION

The present invention relates to methods for producing chewing gum. More particularly the invention relates to producing chewing gum containing an antimicrobial agent. The antimicrobial agent that is added to the chewing gum is treated to control its rate of release in the chewing gum.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. Antimicrobial agents may be added to gum; however, antimicrobial agents may vary in their release rate. Some that are not water soluble may be encapsulated in a water soluble matrix such that, during the chewing period, they may be released quickly.

Thus there are specific advantages to adding antimicrobial agents to chewing gum by a controlled release mechanism.

One antimicrobial agent, called triclosan, used in a wide variety of oral compositions, is disclosed in U.S. Pat. Nos. 4,894,220; 5,156,835; 5,300,305; 5,453,265; 5,474,761; 5,496,540; and 5,531,982. The use of triclosan in an oral composition including chewing gum is disclosed in Japanese Patent Publication No. 92-139117 A and in U.S. Pat. Nos. 5,032,385; 5,037,637; 5,334,375; 5,356,615; and 5,472,685.

The use of another antimicrobial agent, hexylresorcinol, in oral compositions is disclosed by U.S. Pat. Nos. 4,853,212 and 5,156,835.

The use of cetylpyridinium chloride as an antimicrobial agent in oral compositions is disclosed in U.S. Pat. Nos. 4,624,849 and 5,560,906, and European Patent Publication No. 0 399 479.

The antimicrobial agent chlorhexidine digluconate may also be used in oral compositions, specifically in chewing gum, as disclosed in Spanish Patent No. 2,015,656.

Although all of these antimicrobial agents are disclosed in chewing gum, their controlled release for increased effectiveness is not disclosed.

SUMMARY OF THE INVENTION

The present invention is a method of producing chewing gum with antimicrobial agents which have been physically modified to control their release. The present invention also relates to the chewing gum so produced. These agents may be added to sucrose type gum formulations, replacing a small quantity of sucrose. The formulation may be a low or high moisture formulation containing low or high amounts of moisture containing syrup. These agents may also be used in low or non-sugar gum formulations, replacing a small quantity of sorbitol, mannitol, other polyols or carbohydrates. Non-sugar formulations may include low or high moisture sugar free chewing gums.

Antimicrobial agents may be combined or co-dried with bulk sweeteners typically used in chewing gum, such as sucrose, dextrose, fructose and maltodextrins, as well as sugar alcohols such as sorbitol, mannitol, xylitol, maltitol, lactitol, hydrogenated isomaltulose and hydrogenated starch hydrolyzates.

The modified release rate noted above may be a fast release or a delayed release. The modified release of antimicrobial agents is obtained by encapsulation, partial encapsulation or partial coating, entrapment or absorption with high or low water soluble materials or water insoluble materials. The procedures for modifying the antimicrobial agents include spray drying, spray chilling, fluid bed coating, coacervation, extrusion and other agglomerating and standard encapsulating techniques. Antimicrobial agents may also be absorbed onto an inert or water-insoluble material. Antimicrobial agents may be modified in a multiple step process comprising any of the processes, or a combination of the processes noted. Prior to encapsulation, antimicrobial agents may also be combined with bulk sweeteners including sucrose, dextrose, fructose, maltodextrin or other bulk sweeteners, as well as sugar alcohols such as sorbitol, mannitol, xylitol, maltitol, lactitol, hydrogenated isomaltulose and hydrogenated starch hydrolyzates.

Prior to encapsulation, antimicrobial agents may be combined with high-intensity sweeteners, including but not limited to thaumatin, aspartame, alitame, acesulfame K, saccharin acid and its salts, glycyrrhizin, cyclamate and its salts, stevioside and dihydrochalcones. Co-encapsulation of antimicrobial agents along with a high-intensity sweetener may improve the taste quality of the antimicrobial agent and control the sweetener release with the agent. This can improve the quality of the gum product and increase consumer acceptability.

Preferable antimicrobial agents include

1) TRICLOSAN (2,4,4-trichloro-2-hydroxydiphenyl ether),
2) cetylpyridinium chloride, 3) hexylresorcinol, and
4) chlorhexidine digluconate.

DETAILED DESCRIPTION OF THE PREFERRED EMBODIMENTS

In the context of this invention, chewing gum refers to chewing gum, bubble gum and the like. Moreover, all percentages are based on weight percentages unless otherwise specified. Further, although some terms are referred to in the singular, it is understood that coated products often contain multiple layers of coating. Therefore a phrase that refers to "the coating," refers to one or more layers of coating. Finally, all references cited herein are incorporated by reference.

As discussed previously, there are a wide variety of antimicrobial agents which can be used in oral compositions. Some of the preferred antimicrobial agents are 1) TRICLOSAN (2,4,4-trichloro-2-hydroxydiphenyl ether), 2) cetylpyridinium chloride, 3) hexylresorcinol, and 4) chlorhexidine digluconate. Among these, the most preferred is chlorhexidine digluconate.

Most of the antimicrobial agents vary in their water solubility. Some solubilities are:

Triclosan—about 0.05% at 25° C.
Hexylresorcinol—about 0.05% at 25° C.
Chlorhexidine digluconate—50% at 25° C.
Cetylpyridinium chloride—33% at 25° C.

In some instances, the water soluble agents which release readily from chewing gum may be modified by encapsulation to give an even faster release from chewing gum. However, in most instances the water soluble agents would be encapsulated or entrapped to give a delayed release from gum.

Other antimicrobial agents that are not very water soluble may release slowly and may not be as effective. As a result, encapsulation for fast release may be desired for these antimicrobial agents. Other agents may have a moderate release and these may be entrapped to give a much longer delayed release.

Levels of antimicrobial agents will vary according to their effectiveness. Generally, antimicrobial agents will be used in gum at about 0.01% to about 5% and preferably about 0.05% to about 2%. Most preferably, levels of 0.1% to about 1.0% should be used in chewing gum.

Water soluble antimicrobial agents can be added to chewing gum as a powder, as an aqueous dispersion, or dispersed in glycerin, propylene glycol, corn syrup, hydrogenated starch hydrolyzate, or any other compatible aqueous dispersion. Water insoluble agents can be added to chewing gum as a powder or with flavors, emulsifiers or organic softeners.

For aqueous dispersions, an emulsifier can also be mixed in the solution with the antimicrobial agents and the mixture added to a chewing gum. A flavor can also be added to the antimicrobial agents/emulsifier mixture. The emulsion formed can be added to chewing gum. Antimicrobial agents in powder form may also be mixed into a molten chewing gum base during base manufacture or prior to manufacture of the gum. Antimicrobial agents may also be mixed with base ingredients during base manufacture.

As stated previously, antimicrobial agents release at various rates from chewing gum during the early stages of mastication of the gum because of their varying solubility in water. Physical modifications of the antimicrobial agent by encapsulation with highly water soluble substrates will increase their release in chewing gum by increasing the solubility or dissolution rate. Any standard technique which gives partial or full encapsulation can be used. These techniques include, but are not limited to, spray drying, spray chilling, fluid-bed coating and coacervation. These encapsulation techniques may be used individually in a single step process or in any combination in a multiple step process. The preferred technique for fast release of antimicrobial agents is spray drying.

Antimicrobial agents may also be encapsulated or entrapped to give a delayed release from chewing gum. Antimicrobial agents may be encapsulated with sweeteners, specifically high-intensity sweeteners such as thaumatin, dihydrochalcones, acesulfame K, aspartame, sucralose, alitame, saccharin and cyclamates to give improved taste when the antimicrobial agent is released.

The encapsulation techniques described herein are standard coating techniques and generally give varying degrees of coating from partial to full coating, depending on the coating composition used in the process. Generally, compositions that have high organic solubility, good film-forming properties and low water solubility give better delayed release, while compositions that have high water solubility give better fast release. Such low water-solubility compositions include acrylic polymers and copolymers, carboxyvinyl polymer, polyamides, polystyrene, polyvinyl acetate, polyvinyl acetate phthalate, polyvinylpyrrolidone and waxes. Although all of these materials are possible for encapsulation of antimicrobial agents, only food-grade materials should be considered. Two standard food-grade coating materials that are good film formers but not water soluble are shellac and Zein. Others which are more water soluble, but good film formers, are materials like agar, alginates, a wide range of cellulose derivatives like ethyl cellulose, methyl cellulose, sodium hydroxymethyl cellulose, and hydroxypropylmethyl cellulose, dextrin, gelatin, and modified starches. These ingredients, which are generally approved for food use, may give a fast release when used as an encapsulant for antimicrobial agents. Other encapsulants like acacia or maltodextrin can also encapsulate antimicrobial agents and give a fast release rate from gum.

The amount of coating or encapsulating material on the antimicrobial agents may also control the length of time for its release from chewing gum. Generally, the higher the level of coating and the lower the amount of active antimicrobial agents, the slower the release during mastication with low water soluble compositions. The release rate is generally not instantaneous, but gradual over an extended period of time. To obtain the delayed release to blend with a gum's flavor release, the encapsulant should be a minimum of about 20% of the coated antimicrobial agents. Preferably, the encapsulant should be a minimum of about 30% of the coated antimicrobial agents, and most preferably should be a minimum of about 40% of the coated antimicrobial agents. Depending on the coating material, a higher or lower amount of coating material may be needed to give the desired release.

Another method of giving a modified release of antimicrobial agents is agglomeration with an agglomerating agent which partially coats the antimicrobial agents. This method includes the step of mixing antimicrobial agents and an agglomerating agent with a small amount of water or other solvent. The mixture is prepared in such a way as to have individual wet particles in contact with each other so that a partial coating can be applied. After the water or solvent is removed, the mixture is ground and used as a powdered, coated antimicrobial agent.

Materials that can be used as the agglomerating agent are the same as those used in encapsulation mentioned previously. However, since the coating is only a partial encapsulation, some agglomerating agents are more effective in increasing the antimicrobial agents release than others. Some of the better agglomerating agents for delayed release are the organic polymers like acrylic polymers and copolymers, polyvinyl acetate, polyvinylpyrrolidone, waxes, shellac and Zein. Other agglomerating agents are not as effective in giving a delayed release as are the polymers, waxes, shellac and Zein, but can be used to give some delayed release. Other agglomerating agents that give a fast release include, but are not limited to, agar, alginates, a wide range of water soluble cellulose derivatives like ethyl cellulose, methyl cellulose, sodium hydroxymethyl cellulose, hydroxypropylmethyl cellulose, dextrin, gelatin, modified starches, and vegetable gums like guar gum, locust bean gum and carrageenan. Even though the agglomerated antimicrobial agent is only partially coated, when the quantity of coating is increased compared to the quantity of antimicrobial agent, the release of antimicrobial agent can also be modified for mastication. The level of coating used in the agglomerated product is a minimum of about 5%.

Preferably, the coating level is a minimum of about 15% and more preferably about 20%. Depending on the agglomerating material, a higher or lower amount of material may be needed to give the desired release of antimicrobial agent.

Antimicrobial agents may be coated in a two-step process or a multiple step process. Antimicrobial agents may be encapsulated with any of the materials as described previously and then the encapsulated antimicrobial agents can be agglomerated as previously described to obtain an encapsulated/agglomerated/antimicrobial agent product that could be used in chewing gum to give a delayed release of the antimicrobial agent.

In another embodiment of this invention, antimicrobial agents may be absorbed onto another component which is porous and become entrapped in the matrix of the porous component. Common materials used for absorbing antimicrobial agents include, but are not limited to, silicas, silicates, pharmasorb clay, spongelike beads or microbeads, amorphous carbonates and hydroxides, including aluminum and calcium lakes, all of which result in a delayed release of antimicrobial agents. Other water soluble materials including amorphous sugars such as spray-dried dextrose, sucrose, alditols and vegetable gums and other spray-dried materials result in a faster release of antimicrobial agents.

Depending on the type of absorbent materials and how it is prepared, the amount of antimicrobial agents that can be loaded onto the absorbent will vary. Generally materials like polymers or spongelike beads or microbeads, amorphous sugars and alditols and amorphous carbonates and hydroxides absorb about 10% to about 40% of the weight of the absorbent. Other materials like silicas and pharmasorb clays may be able to absorb about 20% to about 80% of the weight of the absorbent.

The general procedure for absorbing an antimicrobial agent onto the absorbent is as follows. An absorbent like fumed silica powder can be mixed in a powder blender and an aqueous solution of an antimicrobial agent can be sprayed onto the powder as mixing continues. The aqueous solution can be about 10% to 30% solids, and higher solid levels may be used if temperatures up to 90° C. are used. Generally water is the solvent, but other solvents like alcohol could also be used if approved for use in food. As the powder mixes, the liquid is sprayed onto the powder. Spraying is stopped before the mix becomes damp. The still free-flowing powder is removed from the mixer and dried to remove the water or other solvent, and is then ground to a specific particle size.

After the antimicrobial agent is absorbed or fixed onto an absorbent, the fixative/inhibitor can be coated by encapsulation. Either full or partial encapsulation may be used, depending on the coating composition used in the process. Full encapsulation may be obtained by coating with a polymer as in spray drying, spray chilling, fluid-bed coating, coacervation, or any other standard technique. A partial encapsulation or coating can be obtained by agglomeration of the fixative antimicrobial mixture using any of the materials discussed above.

Another form of encapsulation is by entrapment of an ingredient by fiber extrusion or fiber spinning into a polymer. Polymers that can be used for extrusion are PVAC, hydroxypropyl cellulose, polyethylene and other types of plastic polymers. A process of encapsulation by fiber extrusion is disclosed in U.S. Pat. No. 4,978,537, which is hereby incorporated by reference. The water insoluble polymer may be preblended with the antimicrobial agent prior to fiber extrusion, or may be added after the polymer is melted. As the extrudate is extruded, it results in small fibers that are cooled and ground. This type of encapsulation/entrapment generally gives a very long, delayed release of an active ingredient.

The four primary methods to obtain a modified release of the antimicrobial agent are: (1) encapsulation by spray drying, fluid-bed coating, spray chilling and coacervation to give full or partial encapsulation, (2) agglomeration to give partial encapsulation, (3) fixation or absorption which also gives partial encapsulation, and (4) entrapment into an extruded compound. These four methods, combined in any usable manner which physically modifies the release or dissolvability of the antimicrobial agent, are included in this invention.

A method of modifying the release rate of the antimicrobial agents from the chewing gum is to add the antimicrobial agents to the dusting compound of a chewing gum. A rolling or dusting compound may be applied to the surface of chewing gum as it is formed. This rolling or dusting compound serves to reduce sticking of the chewing gum product to machinery as it is formed and as it is wrapped, and sticking of the product to its wrapper after it is wrapped and is being stored. The rolling compound comprises an antimicrobial agent powder in combination with mannitol, sorbitol, sucrose, starch, calcium carbonate, talc, other orally acceptable substances or a combination thereof. The rolling compound constitutes from about 0.25% to about 10%, but preferably about 1% to about 3% by weight of the chewing gum composition. The amount of an antimicrobial agent powder added to the rolling compound is about 0.05% to about 10% of the rolling compound or about 5 ppm to about 1000 ppm of the chewing gum composition. This method of using an antimicrobial agent powder in the chewing gum allows for a lower usage level of the antimicrobial agent, gives an antimicrobial agent a fast release rate, eliminates absorption by the gum base, and reduces or eliminates any possible reaction with gum base, flavor components, or other components, yielding improved shelf stability.

Another method of modifying the release rate of an antimicrobial agent is to use it in the coating/panning of a pellet chewing gum. Pellet or ball gum is prepared as conventional chewing gum, but formed into pellets that are pillow shaped or into balls. The pellets/balls can then be sugar coated or panned by conventional panning techniques to make a unique sugar coated pellet gum. Some antimicrobial agents may generally be very stable and water soluble and can be easily dispersed in a sugar solution prepared for sugar panning. Other non-soluble antimicrobial agents can be added to flavors used in the coating or added as a powder blended with other powders often used in some types of conventional panning procedures. Using an antimicrobial agent in a coating isolates it from other gum ingredients and modifies its release rate in chewing gum. Levels of an antimicrobial agent may be about 100 ppm (0.01%) to about 25,000 ppm (2.5%) in the coating and about 50 ppm (0.005%) to about 10,000 ppm (1%) of the weight of the chewing gum product. The weight of the coating may be about 20% to about 50% of the weight of the finished gum product.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, hydrogenated isomaltulose and other new alditols or a combination thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate and talc. Antitack agents may also be added as panning modifiers which allow for the use of a variety of carbohydrates and sugar alcohols in the development of new panned or coated gum products. Flavors may also be added with the sugar coating and with antimicrobial agents to yield unique product characteristics.

Another type of pan coating would also modify the release rate of antimicrobial agents from the chewing gum. This technique is referred to as film coating and is more common in pharmaceuticals than in chewing gum, but procedures are similar. A film like shellac, Zein, or cellulose-type material is applied onto a pellet-type product forming a thin film on the surface of the product. The film is applied by mixing the polymer, a plasticizer and a solvent (pigments are optional) and spraying the mixture onto the pellet surface. This is done in conventional type panning equipment, or in more advanced side-vented coating pans. When a solvent like alcohol is used, extra precautions are needed to prevent fires and explosions, and specialized equipment must be used.

Some film polymers can use water as the solvent in film coating. Recent advances in polymer research and in film coating technology eliminates the problem associated with the use of flammable solvents in coating. These advances make it possible to apply aqueous films to a pellet or chewing gum product. Since some antimicrobial agents are water soluble, they may be added to this aqueous film solution and applied with the film to the pellet or chewing gum product. The aqueous film, or even the alcohol solvent film, in which antimicrobial agents are dispersed may also contain a flavor along with the polymer and plasticizer.

The previously described encapsulated, agglomerated or absorbed antimicrobial agents may readily be incorporated into a chewing gum composition. The remainder of the chewing gum ingredients are noncritical to the present invention. That is, the coated particles of antimicrobial agents can be incorporated into conventional chewing gum formulations in a conventional manner. Coated antimicrobial agents may be used in a sugar chewing gum or a sugarless chewing gum. The coated antimicrobial agents may be used in either regular chewing gum or bubble gum.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, waxes, softeners and inorganic fillers. Elastomers may include polyisobutylene, isobutylene-isoprene copolymer and styrene butadiene rubber, as well as natural latexes such as chicle. Resins include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnauba. According to the preferred embodiment of the present invention, the insoluble gum base constitutes between about 5% and about 95% by weight of the gum. More preferably the insoluble gum base comprises between about 10% and about 50% by weight of the gum, and most preferably between about 20% and about 35% by weight of the gum.

The gum base typically also includes a filler component. The filler component may be calcium carbonate, magnesium carbonate, talc, dicalcium phosphate or the like. The filler may constitute between about 5% and about 60% by weight of the gum base. Preferably, the filler comprises about 5% to about 50% by weight of the gum base.

Gum bases typically also contain softeners, including glycerol monostearate and glycerol triacetate. Further, gum bases may also contain optional ingredients such as antioxidants, colors, and emulsifiers. The present invention contemplates employing any commercially acceptable gum base.

The water-soluble portion of the chewing gum may further comprise softeners, sweeteners, flavoring agents and combinations thereof. Softeners are added to the chewing gum in order to optimize the chewability and mouth feel of the gum. Softeners, also known in the art as plasticizers or plasticizing agents, generally constitute between about 0.5% and about 15% by weight of the chewing gum. Softeners contemplated by the present invention include glycerin, lecithin and combinations thereof. Further, aqueous sweetener solutions such as those containing sorbitol, hydrogenated starch hydrolyzates, corn syrup and combinations thereof may be used as softeners and binding agents in gum.

As mentioned above, the coated antimicrobial agent of the present invention may be used in sugar or sugarless gum formulations. Sugar sweeteners generally include saccharide-containing components commonly known in the chewing gum art which comprise, but are not limited to, sucrose, dextrose, maltose, dextrin, dried invert sugar, fructose, levulose, galactose, corn syrup solids and the like, alone or in any combination. Sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol and the like, alone or in any combination.

Depending on the particular antimicrobial agent release profile and shelf-stability needed, the coated antimicrobial agent of the present invention can also be used in combination with uncoated high-potency sweeteners or with high-potency sweeteners coated with other materials and by other techniques.

A flavoring agent may also be present in the chewing gum in an amount within the range of from about 0.1% to about 15%, preferably from about 0.5% to about 3%, by weight of the gum. The flavoring agents may comprise essential oils, synthetic flavors, or mixtures thereof including, but not limited to oils derived from plants and fruits such as citrus oils, fruit essences, peppermint oil, spearmint oil, clove oil, oil of wintergreen, anise, and the like. Artificial flavoring components are also contemplated for use in gums of the present invention. Those skilled in the art will recognize that natural and artificial flavoring agents may be combined in any sensorally acceptable blend. All such flavors and flavor blends are contemplated by the present invention.

Optional ingredients such as colors, emulsifiers and pharmaceutical agents may be added to the chewing gum.

In general, chewing gum is manufactured by sequentially adding the various chewing gum ingredients to a commercially available mixer known in the art. After the ingredients have been thoroughly mixed, the gum mass is discharged from the mixer and shaped into the desired form such as by rolling into sheets and cutting into sticks, extruding into chunks or casting into pellets.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further portions of the bulking agent may then be added to the mixer. A flavoring agent is typically added with the final portion of the bulking agent. The coated antimicrobial agent of the present invention is preferably added after the final portion of bulking agent and flavor have been added.

The entire mixing procedure typically takes from five to fifteen minutes, but longer mixing times may sometimes be required. Those skilled in the art will recognize that many variations of the above described procedure may be followed.

EXAMPLES

The following examples of the invention and comparative examples are provided by way of explanation and illustration.

The formulas listed in Table 1 comprise various sugar formulas in which the antimicrobial agent chlorhexidine digluconate can be added to gum after the chlorhexidine is dissolved in various aqueous type solvents.

TABLE 1

| (Wt. %) | | | | | | |
|---|---|---|---|---|---|---|
| | Example 1 | Example 2 | Example 3 | Example 4 | Example 5 | Example 6 |
| Sugar | 62.2 | 61.9 | 60.8 | 60.8 | 60.8 | 58.3 |
| Gum Base | 19.2 | 19.2 | 19.2 | 19.2 | 19.2 | 19.2 |
| Glycerin | 1.4 | 1.4 | 0.0 | 0.0 | 0.0 | 1.4 |
| Corn Syrup | 15.9 | 15.9 | 12.9 | 12.9 | 12.9 | — |
| Lecithin | 0.2 | 0.2 | 0.2 | 0.2 | 0.2 | 0.2 |
| Peppermint Flavor | 0.9 | 0.9 | 0.9 | 0.9 | 0.9 | 0.9 |
| Liquid/ Chlorhexidine digluconate blend | 0.2 | 0.5 | 6.0 | 6.0 | 6.0 | 20.0 |

Example 1 and 2

Chlorhexidine digluconate powder can be added directly to the gum.

Example 3

A 1.0 gram portion of chlorhexidine digluconate can be dissolved in 99.0 grams of hot water, making a 20.0% solution, and added to gum.

Example 4

A 0.5 gram portion of chlorhexidine digluconate can be dissolved in 99.5 grams of hot propylene glycol, making a 5.0% solution, and added to gum.

Example 5

A 0.5 gram portion of chlorhexidine digluconate can be dissolved in 99.5 grams of hot glycerin, making a 5.0% solution, and added to gum.

Example 6

A 1.0 gram portion of chlorhexidine digluconate can be dissolved in hot corn syrup, making a 2.5% solution, and added to gum.

In the next examples of a sugar gum formulation, chlorhexidine digluconate can be dissolved in hot water and emulsifiers can be added to the aqueous solution. Example solutions can be prepared by dissolving 5 grams of chlorhexidine digluconate in 95 grams hot water and adding 5 grams of emulsifiers of various hydrophilic-lipophilic balance (HLB) values to the solution. The mixtures can then be used in the following formulas.

TABLE 2

| (WT. %) | | | | | | |
|---|---|---|---|---|---|---|
| | Example 7 | Example 8 | Example 9 | Example 10 | Example 11 | Example 12 |
| Sugar | 50.7 | 50.7 | 50.7 | 50.7 | 50.7 | 50.7 |
| Base | 19.2 | 19.2 | 19.2 | 19.2 | 19.2 | 19.2 |
| Corn Syrup | 12.9 | 12.9 | 12.9 | 12.9 | 12.9 | 12.9 |
| Glycerin | 1.4 | 1.4 | 1.4 | 1.4 | 1.4 | 1.4 |
| Dextrose Monohydrate | 9.9 | 9.9 | 9.9 | 9.9 | 9.9 | 9.9 |
| Peppermint Flavor | 0.9 | 0.9 | 0.9 | 0.9 | 0.9 | 0.9 |
| Chlorhexidine digluconate/ Emulsifier Water Mixture | 5.0 | 5.0 | 5.0 | 5.0 | 5.0 | 5.0 |
| | None | HLB = 2 | HLB = 4 | HLB = 6 | HLB = 9 | HLB = 12 |

Examples 13–18

The same as the formulations made in Examples 7–12, respectively, except that the flavor can be mixed together with the antimicrobial agent emulsion and emulsified before adding the mixture to the gum batch.

Chlorhexidine digluconate can also be blended into various base ingredients. A typical base formula is as follows:

| | Wt. % |
|---|---|
| Polyvinyl acetate | 27 |
| Synthetic rubber | 13 |
| Paraffin Wax | 13 |
| Fat | 3 |
| Glycerol Monostearate | 5 |
| Terpene Resin | 27 |
| Calcium Carbonate Filler | 12 |
| | 100% |

The individual base components can be softened prior to their addition in the base manufacturing process. To the presoftened base component, chlorhexidine digluconate can be added and mixed, and then the presoftened base/ chlorhexidine digluconate blend can be added to make the finished base. In the following examples, chlorhexidine digluconate can be mixed first with one of the base ingredients, and the mixed ingredient can then be used in making a base. The ingredients blended with chlorhexidine digluconate can then be used at the levels indicated in the typical base formula above.

Example 19

The terpene resin used to make the base is 98% polyterpene resin and 2% chlorhexidine digluconate.

Example 20

The polyvinyl acetate used to make the base is 98% low M.W. polyvinyl acetate and 2% chlorhexidine digluconate.

Example 21

The paraffin wax used to make the base is 96% paraffin wax and 4% chlorhexidine digluconate.

Chlorhexidine digluconate may also be added to an otherwise complete gum base.

Example 22

0.5% chlorhexidine digluconate can be mixed with 99.5% of a gum base having the above listed typical formula. The chlorhexidine digluconate can be added near the end of the process after all the other ingredients are added.

The samples of finished base made with chlorhexidine digluconate added to different base components can then be evaluated in a sugar-type chewing gum formulated as follows:

TABLE 3

(Wt. %)

(For examples 19, 20, 21, and 22)

| | |
|---|---|
| Sugar | 55.2 |
| Base | 19.2 |
| Corn Syrup | 13.4 |
| Glycerine | 1.4 |
| Dextrose Monohydrate | 9.9 |
| Peppermint Flavor | 0.9 |
| | 100% |

The theoretical level of chlorhexidine digluconate in the finished gum is 0.1%.

Using the following formulation of a sugar or sugar-free gum, a variety of encapsulated chlorhexidine digluconate samples can be evaluated:

TABLE 4

(Wt. %)

| | Sugar Free | Sugar |
|---|---|---|
| Sorbitol | 49.4 | — |
| Sugar | — | 55.3 |
| Mannitol | 8.0 | — |
| Gum Base | 25.5 | 20.0 |
| Glycerin | 8.5 | 1.4 |
| Corn Syrup | — | 12.0 |
| Lycasin brand Hydrogenated Starch Hydrolyzates | 6.8 | — |
| Dextrose Monohydrate | — | 10.0 |
| Peppermint Flavor | 1.4 | 0.9 |
| Active Chlorhexidine digluconate | 0.4% | 0.4% |

For spray drying, the solids level of an aqueous or alcoholic solution can be about 5–30%, but preferred levels are indicated in the examples listed.

Example 23

An 80% shellac, 20% active chlorhexidine digluconate powder mixture is obtained by spray drying an alcohol/shellac/chlorhexidine digluconate solution at total solids of 20%.

Example 24

A 50% shellac, 50% active chlorhexidine digluconate powder mixture is obtained by spray drying an appropriate ratio of alcohol/shellac/chlorhexidine digluconate solution at 20% solids.

Example 25

A 70% Zein, 30% active chlorhexidine digluconate powder mixture is obtained by spray drying an alcohol/Zein/chlorhexidine digluconate solution at 10% solids.

Example 26

A 40% shellac, 60% active chlorhexidine digluconate powder mixture is obtained by fluid-bed coating chlorhexidine digluconate with an alcohol/shellac solution at 30% solids.

Example 27

A 60% shellac, 40% active chlorhexidine digluconate powder mixture is obtained by fluid-bed coating chlorhexidine digluconate with an alcohol/shellac solution at 30% solids.

Example 28

A 40% Zein, 60% active chlorhexidine digluconate powder mixture is obtained by fluid-bed coating chlorhexidine digluconate with an alcohol/Zein solution at 25% solids.

Example 29

An 85% wax, 15% active chlorhexidine digluconate powder mixture is obtained by spray chilling a mixture of molten wax and chlorhexidine digluconate.

Example 30

A 70% wax, 30% active chlorhexidine digluconate powder mixture is obtained by spray chilling a mixture of molten wax and chlorhexidine digluconate.

Example 31

A 70% Zein, 30% active chlorhexidine digluconate powder mixture is obtained by spray drying a hot aqueous mixture of chlorhexidine digluconate and Zein dispersed in an aqueous, high-pH (pH of 11.6–12.0) media at 10% solids.

Example 32

A 20% Zein, 80% active chlorhexidine digluconate powder mixture is obtained by fluid-bed coating chlorhexidine digluconate with an aqueous, high-pH (pH=11.6–12.0) Zein dispersion of 10% solids.

Example 33

A 20% Zein, 20% shellac, 60% active chlorhexidine digluconate powder mixture is obtained by spray drying an alcohol/shellac/chlorhexidine digluconate mixture and then fluid-bed coating the spray dried product for a second coating of alcohol and Zein.

Examples 23 to 33 would all give nearly complete encapsulation and would delay the release of chlorhexidine digluconate when used in the sugar or sugarless gum formulations in Table 4. The higher levels of coating would give a longer delayed release of chlorhexidine digluconate than the lower levels of coating.

Other polymers that are more water soluble and used in coating would have a slower release of the chlorhexidine digluconate.

Example 34

An 80% gelatin, 20% active chlorhexidine digluconate powder mixture is obtained by spray drying a hot gelatin/chlorhexidine digluconate solution at 20% solids.

Example 35

A 30% hydroxypropylmethyl cellulose (HPMC), 70% chlorhexidine digluconate powder mixture is obtained by fluid-bed coating chlorhexidine digluconate with an aqueous solution of HPMC at 10% solids.

Example 36

A 50% maltodextrin, 50% active chlorhexidine digluconate powder mixture is obtained by spray drying a hot aqueous solution of chlorhexidine digluconate and maltodextrin at 30% solids.

Example 37

A 40% gum arabic, 60% active chlorhexidine digluconate powder mixture is obtained by fluid-bed coating chlorhexidine digluconate with an aqueous solution of gum arabic at 30% solids.

The coated chlorhexidine digluconate from Examples 34 and 35, when used in the chewing gum formulas in Table 4, would give a slightly slow release of chlorhexidine digluconate. The product coated with maltodextrin and gum arabic in Examples 36 and 37, when used in the gum formulas in Table 4, would show a fast release of chlorhexidine digluconate in chewing gum.

Chlorhexidine digluconate could also be used in gum as an agglomerated chlorhexidine digluconate to give fast or delayed chlorhexidine digluconate release. Agglomerated chlorhexidine digluconate can be prepared as in the following examples:

Example 38

A 15% hydroxypropylmethyl cellulose (HPMC), 85% active chlorhexidine digluconate powder mixture is prepared by agglomerating chlorhexidine digluconate and HPMC blended together, with water being added, and the resulting product being dried and ground.

Example 39

A 15% gelatin, 85% active chlorhexidine digluconate powder mixture is made by agglomerating chlorhexidine digluconate and gelatin blended together, with water being added, and the resulting product being dried and ground.

Example 40

A 10% Zein, 90% active chlorhexidine digluconate powder mixture is made by agglomerating chlorhexidine digluconate with an alcohol solution containing 25% Zein, and drying and grinding the resulting product.

Example 41

A 15% shellac, 85% active chlorhexidine digluconate powder mixture is made by agglomerating chlorhexidine digluconate with an alcohol solution containing 25% shellac, and drying and grinding the resulting product.

Example 42

A 20% HPMC, 80% active chlorhexidine digluconate powder mixture is obtained by agglomerating an HPMC and chlorhexidine digluconate mixture blended together, with water being added, and the resulting product being dried and ground.

Example 43

A 20% Zein, 80% active chlorhexidine digluconate powder mixture is obtained by agglomerating chlorhexidine digluconate and Zein dissolved in high-pH water (11.6–12.0) at 15% solids, with the resulting product being dried and ground.

Example 44

A 20% wax, 80% active chlorhexidine digluconate powder mixture is obtained by agglomerating chlorhexidine digluconate and molten wax, and cooling and grinding the resulting product.

Example 45

A 15% maltodextrin, 85% active chlorhexidine digluconate powder mixture is obtained by agglomerating a blend of chlorhexidine digluconate and maltodextrin, then adding water, drying and grinding.

All of the above mixtures can be added to any of the following types of chewing gum formulas:

TABLE 5

| | (Wt. %) | | | |
|---|---|---|---|---|
| | Sugar | Sugar With Sorbitol | Sugarless With Water | Sugarless With Lycasin | Sugarless No Water |
| Gum Base | 19.2 | 19.2 | 25.5 | 25.5 | 25.5 |
| Sugar | 55.3 | 53.3 | — | — | — |
| Sorbitol | — | 2.0 | 53.3 | 49.0 | 51.8 |
| Mannitol | — | — | 8.0 | 8.0 | 12.0 |
| Corn Syrup | 13.1 | 13.1 | — | — | — |
| Lycasin/Sorbitol liquid | — | — | 9.5[a] | 6.8[b] | — |
| Glycerin | 1.4 | 1.4 | 1.5 | 8.5 | 8.5 |
| Lecithin | — | — | 0.2 | 0.2 | 0.2 |
| Dextrose Monohydrate | 9.9 | 9.9 | — | — | — |
| Flavor | 0.9 | 0.9 | 1.5 | 1.5 | 1.5 |
| Level of Active Chlorhexidine digluconate | 0.2 | 0.2 | 0.5 | 0.5 | 0.5 |

[a]liquid sorbitol (70% sorbitol, 30% water)
[b]hydrogenated starch hydrolyzate syrup If each of the examples of agglomerated material (38–45) were evaluated in the formulations shown in Table 5, most samples would give chlorhexidine digluconate a delayed release. Samples using Zein, wax, and shellac would yield the slowest release rate, whereas samples with HPMC and gelatin would yield the next slowest release. Maltodextrin would give a release compared to chlorhexidine digluconate added directly to the gum.

Partially coated or fully coated chlorhexidine digluconate can also be used in sugar type gum formulations containing other sugars, such as in the following formulations A–G:

TABLE 6

| | (Wt. %) | | | | | | |
|---|---|---|---|---|---|---|---|
| | A | B | C | D | E | F | G |
| Gum Base | 19.2 | 19.2 | 19.2 | 19.2 | 19.2 | 19.2 | 19.2 |
| Sugar | 59.0 | 50.0 | 49.0 | 49.0 | 50.0 | 52.0 | 52.0 |
| Glycerin | 1.4 | 1.4 | 1.4 | 1.4 | 1.4 | 1.4 | 1.4 |
| Corn Syrup | 19.0 | 23.0 | 19.0 | 19.0 | 23.0 | 16.0 | 16.0 |
| Dextrose | — | — | 5.0 | — | — | — | — |
| Lactose | — | — | — | — | 5.0 | — | — |
| Fructose | — | — | 5.0 | — | — | — | — |
| Invert Sugar | — | — | — | 10.0 | — | — | — |
| Maltose | — | — | — | — | — | 10.0 | — |
| Palatinose | — | — | — | — | — | — | 10.0 |
| Corn Syrup Solids | — | 5.0 | — | — | — | — | — |
| Peppermint Flavor | 0.9 | 0.9 | 0.9 | 0.9 | 0.9 | 0.9 | 0.9 |
| Level of Active Chlorhexidine digluconate | 0.5 | 0.5 | 0.5 | 0.5 | 0.5 | 0.5 | 0.5 |

These formulations may also contain sugar alcohols such as sorbitol, mannitol, xylitol, lactitol, maltitol, hydrogenated isomaltulose, and Lycasin or combinations thereof. Sugarless type gum formulations with partially coated or fully coated chlorhexidine digluconate can also be made using various sugar alcohols, such as the following formulations H–P:

TABLE 7

| | (Wt. %) | | | | | | | | |
|---|---|---|---|---|---|---|---|---|---|
| | H | I | J | K | L | M | N | O | P |
| Base | 25.5 | 25.5 | 25.5 | 25.5 | 25.5 | 25.5 | 25.5 | 25.5 | 25.5 |
| Sorbitol | 53.5 | 46.5 | 41.5 | 41.5 | 41.5 | 41.5 | 36.5 | 37.5 | 46.5 |
| Sorbitol Liquid/Lycasin | 17.0 | 14.0 | 6.0 | — | 5.0 | — | — | 6.0(a) | 18.0(a) |
| Mannitol | — | 10.0 | 8.0 | 8.0 | 8.0 | 8.0 | 8.0 | 8.0 | 8.0 |
| Maltitol | — | — | — | 5.0 | — | — | 5.0 | — | — |
| Xylitol | — | — | 15.0 | 10.0 | — | — | 5.0 | 15.0 | — |
| Lactitol | — | — | — | — | 10.0 | — | — | — | — |
| Hydrogenated Isomaltulose | — | — | — | — | — | 15.0 | 10.0 | — | — |
| Glycerin | 2.0 | 2.0 | 2.0 | 8.0 | 8.0 | 8.0 | 8.0 | 6.0 | — |
| Flavor | 1.5 | 1.5 | 1.5 | 1.5 | 1.5 | 1.5 | 1.5 | 1.5 | 1.5 |
| Level of Active Chlorhexidine digluconate | 0.5 | 0.5 | 0.5 | 0.5 | 0.5 | 0.5 | 0.5 | 0.5 | 0.5 |

(a)Lycasin, all others use sorbitol liquid

All of these formulations in Table 6 and Table 7 which use the agglomerated chlorhexidine digluconate as described in the examples (38–45) and in the previous encapsulated examples (23–35) would be expected to give a delayed release of chlorhexidine digluconate compared to a product made by adding chlorhexidine digluconate directly to gum as a powder.

Multiple step agglomeration/encapsulation procedures can also be used in making release-modified chlorhexidine digluconate for use in the formulations in Tables 5, 6 and 7. Examples of multiple step treatments are here described:

Example 46

Chlorhexidine digluconate is spray dried with maltodextrin at 30% solids to prepare a powder. This powder is then agglomerated with a hydroxypropylmethyl cellulose (HPMC) in a ratio of 85/15 powder/HPMC, wetted with water and dried. After grinding the resulting powder will contain about 68% active chlorhexidine digluconate, 17% maltodextrin and 15% HPMC.

Example 47

Chlorhexidine digluconate is agglomerated with HPMC in a ratio of 85/15 chlorhexidine digluconate/HPMC. After drying and grinding, the resulting powder is fluid-bed coated with an alcohol/shellac solution at about 25% solids to give a final product containing about 60% active chlorhexidine digluconate, 10% HPMC, and about 30% shellac.

Example 48

Chlorhexidine digluconate is agglomerated with HPMC in a ratio of 85/15 chlorhexidine digluconate/HPMC. After drying and grinding, the resulting powder is agglomerated with a 15% solids, high-pH, aqueous solution of Zein to give a final product containing about 60% active chlorhexidine digluconate, 10% HPMC, and 30% Zein.

Example 49

Chlorhexidine digluconate is spray dried with a 25% solution of gelatin. The spray dried product is then agglomerated with a 15% solids, high-pH, aqueous solution of Zein. The final product will contain about 50% active chlorhexidine digluconate, 20% gelatin, and 30% Zein.

Example 50

Chlorhexidine digluconate is agglomerated with molten wax in a ratio of 85/15 chlorhexidine digluconate/wax. When the mixture cools and is ground, it is fluid-bed coated with a 25% Zein-75% alcohol solution, giving a final product containing 60% active chlorhexidine digluconate, 10% wax and 30% Zein.

These examples 46–50, when used in any of the formulations noted in Tables 5, 6, and 7 above, give chlorhexidine digluconate a delayed release. These multiple step procedures can actually give more delayed release than the single step processes. Multiple step processes of more than two steps may give even longer delayed release times, but may generally become less cost effective and less efficient. Preferably, spray drying can be the first step with additional steps of fluid-bed coating, spray chilling and agglomeration being part of the latter steps.

For absorption type examples, the delayed release rate of chlorhexidine digluconate is dependent on the type of absorbing material. Most materials like silicas, silicates, cellulose, carbonates, and hydroxides would be expected to give a more delayed release than amorphous sugar and sugar alcohols. Some examples:

Example 51

A 20% solution of chlorhexidine digluconate is sprayed onto a precipitated silica to absorb the chlorhexidine digluconate. The mixture is dried and ground and the final product is about 50% active chlorhexidine digluconate.

Example 52

A 20% solution of chlorhexidine digluconate is sprayed onto a pharmasorb clay. The mixture is dried and ground and gives a final product of about 80% clay and 20% active chlorhexidine digluconate.

Example 53

A 20% solution of chlorhexidine digluconate is sprayed onto a microcrystalline cellulose powder. The mixture is dried and ground and gives a product that is about 70% microcrystalline cellulose and 30% active chlorhexidine digluconate.

Example 54

A 20% solution of chlorhexidine digluconate is sprayed onto a high absorption starch. The mixture is dried and ground and gives a product that is about 80% starch and 20% active chlorhexidine digluconate.

Example 55

A 20% solution of chlorhexidine digluconate is sprayed onto a calcium carbonate powder. The mixture is dried and ground and gives a product of about 90% calcium carbonate and 10% active chlorhexidine digluconate.

Example 56

A 20% solution of chlorhexidine digluconate is sprayed onto a highly absorptive dextrose material. The mixture is dried and ground and gives a product of about 80% dextrose and 20% active chlorhexidine digluconate.

Example 57

A 20% solution of chlorhexidine digluconate is sprayed onto a sorbitol powder to absorb the material. The mixture is dried and ground and gives a product of about 90% sorbitol and 10% active chlorhexidine digluconate.

The samples prepared in examples 51–57 can be used in gum formulations as noted in Tables 5, 6, and 7. Those preparations which have chlorhexidine digluconate absorbed onto a material that is not water soluble are expected to give a delayed release and those that are water soluble are expected to give fast release.

Another modification or absorption technique is to dry the chlorhexidine digluconate together with a sugar or sugar alcohol, or resolidify the chlorhexidine digluconate with sugar or sugar alcohol when mixed together in a molten state.

Example 58

Chlorhexidine digluconate is added to molten sorbitol in a ratio of 90 parts sorbitol to 10 parts chlorhexidine digluconate. After mixing, the blend is cooled and ground.

Example 59

Chlorhexidine digluconate is added to molten dextrose in a ratio of 90 parts dextrose to 10 parts chlorhexidine digluconate. After mixing, the blend is cooled and ground.

Example 60

4% chlorhexidine digluconate is dissolved in 96% high fructose corn syrup. The mixture is evaporated to a low moisture and ground.

The product of examples 58–60 may be added to the gum formulations shown in Tables 5, 6 and 7.

Many of the examples listed are single step processes. However, more delayed release of the chlorhexidine digluconate may be obtained by combining the various processes of encapsulation, agglomeration, absorption, and entrapment. Any of the preparations made in examples 51–60 can be further treated in fluid-bed coating, spray chilling, or coacervation processes to encapsulate the product, and can be agglomerated with various materials and procedures in a variety of multiple step processes.

The chlorhexidine digluconate can also be used with a variety of high-intensity sweeteners and blended together before encapsulation, agglomeration, absorption, and entrapment. Some examples are:

Example 61

Chlorhexidine digluconate and aspartame are blended together in a 2/1 ratio as a powder. This mixture is then spray chilled with wax in a ratio of 60/40 mixture/wax to obtain a powder containing 40% chlorhexidine digluconate, 20% aspartame, and 40% wax.

Example 62

Chlorhexidine digluconate and thaumatin in a 4/1 ratio are dissolved in water with a 10% solution of gelatin and spray dried. This spray dried powder is then agglomerated with a high-pH aqueous 15% Zein solution. The mixture is dried and ground and gives a product containing 40% chlorhexidine digluconate, 10% thaumatin, 35% gelatin, and 15% Zein.

Example 63

Chlorhexidine digluconate and alitame in a 7/1 ratio are prepared in a 20% solution. This solution is sprayed onto a high absorption silica powder. The mixture is dried, ground and fluid-bed coated with an alcohol/shellac mixture, giving a product that contains 35% chlorhexidine digluconate, 5% alitame, 40% silica, and 20% shellac.

Example 64

Chlorhexidine digluconate and sodium cyclamate in a 1/1 ratio are blended together as a powder and then agglomerated with water and hydroxypropylmethyl cellulose (HPMC). This blend is dried, ground and agglomerated further with a high-pH, aqueous 15% solution of Zein to obtain a product containing 34% sodium cyclamate, 34% chlorhexidine digluconate, 12% HPMC and 20% Zein.

Example 65

Chlorhexidine digluconate and glycyrrhizin in a 1/1 ratio are blended together as a powder and fluid-bed coated with a solution of 25% shellac in alcohol. The coated product is agglomerated further with water and hydroxypropylmethyl cellulose (HPMC) to obtain a product containing 30% chlorhexidine digluconate, 30% glycyrrhizin, 25% shellac, and 15% HPMC.

Example 66

Chlorhexidine digluconate and sodium saccharin in a ratio of 1/1 are blended together as a powder and fluid bed coated with a solution of 25% shellac in alcohol. The coated product is agglomerated further with water and hydroxypropylmethyl cellulose (HPMC) to obtain a product containing 30% chlorhexidine digluconate, 30% sodium saccharin, 25% shellac, and 15% HPMC.

If the blends of chlorhexidine digluconate and other high-intensity sweeteners of examples 61–66 are tested in gum formulations such as those noted in Tables 4, 5, 6 and 7, a significant delayed release of the sweetener and antimicrobial agent would be expected. This delayed release would improve the quality of flavor. The following are examples of fiber extruded PVAC/ chlorhexidine digluconate blends to give a delayed release of chlorhexidine digluconate:

Example 67

Medium molecular weight PVAC and chlorhexidine digluconate at a ratio of 3/1 are blended together as a powder and extruded. The fibers are cooled and ground to give a product containing 75% PVAC and 25% chlorhexidine digluconate.

Example 68

Medium molecular weight PVAC, chlorhexidine digluconate and aspartame at a ratio of 12/4/1 are blended together as a powder and extruded, the resulting fibers are ground and give a product containing 70% PVAC, 24% chlorhexidine digluconate and 6% aspartame.

It should be appreciated that the methods and compositions of the present invention are capable of being incorporated in the form of a variety of embodiments, only a few of which have been illustrated and described above. The invention may be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method of producing a chewing gum product containing a physically-modified antimicrobial agent in order to decrease the release rate of the antimicrobial agent comprising the steps of:
   a) mixing a quantity of an antimicrobial agent with a modifying agent in order to decrease the rate of release of the antimicrobial agent from the chewing gum; and
   b) adding a quantity of the mixture to a chewing gum formulation to provide an antimicrobial agent level in the chewing gum formulation of from about 0.01% to about 5.0%.

2. The method of claim 1 wherein said modifying agent is an encapsulating agent.

3. The method of claim 2 wherein the antimicrobial agent and encapsulating agent are also mixed with a solvent and the resulting mixture is dried prior to being added to the chewing gum.

4. The method of claim 3 wherein the mixture is spray dried and the solvent is selected from the group consisting of alcohol and water.

5. The method of claim 2 wherein the antimicrobial agent is fluid-bed coated with a solution of encapsulating agent and solvent.

6. The method of claim 5 wherein the solvent is selected from the group consisting of alcohol and water.

7. The method of claim 5 wherein the encapsulating agent is selected from the group consisting of shellac and Zein.

8. The method of claim 5 wherein a high-potency sweetener selected from the group consisting of aspartame, alitame, salts of acesulfame, cyclamate and its salts, saccharin and its salts, thaumatin, monellin, dihydrochalcones and combinations thereof is mixed in the mixture in combination with the antimicrobial agent.

9. The method of claim 5 wherein the antimicrobial agent is selected from the group consisting of 1) 2,4,4-trichloro-2-hydroxydiphenyl ether, 2) cetylpyridinium chloride, 3) hexylresorcinol, and 4) chlorhexidine digluconate.

10. The method of claim 2 wherein the antimicrobial agent is encapsulated by coacervation.

11. The method of claim 2 wherein the antimicrobial agent is mixed with a molten encapsulating agent and the antimicrobial agent is encapsulated by spray chilling.

12. The method of claim 11 wherein the encapsulating agent comprises wax.

13. The method of claim 2 wherein the antimicrobial agent is mixed with a polymer as the encapsulating agent and the resulting mixture is extruded into fibers in such a way as to encapsulate the antimicrobial agent.

14. The method of claim 13 wherein the polymer is selected from the group consisting of PVAC, hydroxypropyl cellulose, polyethylene and plastic polymers.

15. The method of claim 1 wherein a high-potency sweetener selected from the group consisting of aspartame, alitame, salts of acesulfame, cyclamate and its salts, saccharine and its salts, thaumatin, monellin, dihydrochalcones and combinations thereof is mixed in the mixture in combination with the antimicrobial agent.

16. The method of claim 1 wherein the antimicrobial agent is selected from the group consisting of 1) 2,4,4-trichloro-2-hydroxydiphenyl ether, 2) cetylpyridinium chloride, 3) hexylresorcinol, and 4) chlorhexidine digluconate.

17. The method of claim 1 wherein the antimicrobial agent is mixed with an absorbent as the modifying agent.

18. A chewing gum product made according to the method of claim 1.

19. A method of producing a chewing gum containing a physically-modified antimicrobial agent in order to decrease the release rate of the antimicrobial agent comprising the steps of:
   a) mixing a quantity of the antimicrobial agent with an agglomerating agent and a solvent to form a mixture in which the agglomerating agent partially coats the antimicrobial agent in order to decrease the rate of release of the antimicrobial agent from the chewing gum;
   b) removing the solvent from the mixture of antimicrobial agent and agglomerating agent to form a dried material; and c) adding a quantity of the dried material to a chewing gum formulation to provide an antimicrobial agent level in gum of from about 0.01% to about 5.0%.

20. The method of claim 19 wherein the level of coating on the agglomerated antimicrobial agent is at least about 5%.

21. The method of claim 19 wherein the level of coating on the agglomerated antimicrobial agent is at least about 15%.

22. The method of claim 19 wherein the level of coating on the agglomerated agent is at least about 20%.

23. The method of claim 19 wherein the dried material is ground to a powder prior to adding the dried material to the chewing gum.

24. The method of claim 19 wherein the agglomerating agent is selected from the group consisting of shellac and Zein.

25. A method of producing a chewing gum product containing a physically-modified antimicrobial agent in order to decrease the release rate of the antimicrobial agent comprising the steps of:

a) mixing a quantity of an antimicrobial agent selected from the group consisting of chlorhexidine digluconate, cetylpyridinium chloride and mixtures thereof with a modifying agent in order to decrease the rate of release of the agent from the chewing gum; and b) adding a quantity of the mixture to a chewing gum formulation to provide an antimicrobial agent level in the chewing gum formulation of from about 0.01% to about 5.0%.

26. The method of claim 25 wherein the antimicrobial agent comprises chlorhexidine digluconate.

* * * * *

UNITED STATES PATENT AND TRADEMARK OFFICE
CERTIFICATE OF CORRECTION

PATENT NO. : 6,592,912 B1
DATED : July 15, 2003
INVENTOR(S) : Roman M. Barabolak et al.

It is certified that error appears in the above-identified patent and that said Letters Patent is hereby corrected as shown below:

<u>Column 21,</u>
Line 2, before "agent" insert -- antimicrobial --.

Signed and Sealed this

Twenty-fifth Day of April, 2006

JON W. DUDAS
*Director of the United States Patent and Trademark Office*